US012804023B2

(12) United States Patent
Lonsberry

(10) Patent No.: US 12,804,023 B2
(45) Date of Patent: Nov. 17, 2026

(54) VIDEO CONFERENCE SYSTEM

(71) Applicant: Carter Lonsberry, Ellington, CT (US)

(72) Inventor: Carter Lonsberry, Ellington, CT (US)

( * ) Notice: Subject to any disclaimer, the term of this patent is extended or adjusted under 35 U.S.C. 154(b) by 172 days.

(21) Appl. No.: 18/544,657

(22) Filed: Dec. 19, 2023

(65) Prior Publication Data

US 2024/0197432 A1 Jun. 20, 2024

Related U.S. Application Data

(60) Provisional application No. 63/433,571, filed on Dec. 19, 2022.

(51) Int. Cl.

| | |
|---|---|
| ***H04L 65/403*** | (2022.01) |
| ***H04N 7/14*** | (2006.01) |
| ***H04N 7/15*** | (2006.01) |
| *A61B 50/33* | (2016.01) |
| *A61B 90/00* | (2016.01) |
| *G16H 40/20* | (2018.01) |
| *G16H 80/00* | (2018.01) |
| *H04L 65/613* | (2022.01) |

(52) U.S. Cl.

CPC ............. *H04L 65/403* (2013.01); *H04N 7/14* (2013.01); *H04N 7/147* (2013.01); *H04N 7/15* (2013.01); *H04N 7/155* (2013.01); *A61B 50/33* (2016.02); *A61B 90/361* (2016.02); *A61B 2090/372* (2016.02); *A61B 2090/373* (2016.02); *A61B 2090/3937* (2016.02); *G16H 40/20* (2018.01); *G16H 80/00* (2018.01); *H04L 65/613* (2022.05)

(58) Field of Classification Search

None

See application file for complete search history.

(56) References Cited

U.S. PATENT DOCUMENTS

| | | | | |
|---|---|---|---|---|
| 6,914,622 | B1 * | 7/2005 | Smith | H04N 7/15 348/E7.083 |
| 8,600,478 | B2 * | 12/2013 | Verard | A61B 90/98 600/407 |
| 8,897,920 | B2 * | 11/2014 | Wang | A61B 34/37 348/14.03 |
| 9,584,760 | B2 * | 2/2017 | Power | H04L 65/611 |
| 2017/0202630 | A1 * | 7/2017 | Gerstner | A61B 50/13 |
| 2019/0095717 | A1 * | 3/2019 | Calmus | G06Q 10/08 |
| 2020/0120308 | A1 * | 4/2020 | McMillan | G06F 3/017 |
| 2021/0279545 | A1 * | 9/2021 | Myers | G06K 19/07781 |
| 2024/0024065 | A1 * | 1/2024 | Okumu | G06V 20/50 |

* cited by examiner

*Primary Examiner* — Quoc D Tran

(74) *Attorney, Agent, or Firm* — Bachman & LaPointe, P.C.

(57) ABSTRACT

A system for video conference communication including a framework supporting a monitor; a processor operatively coupled with the monitor; a camera operatively coupled with the processor, wherein the framework is located in an operating room and the camera is configured to scan at least one of an instrument and an implant; and a microphone and speaker operatively coupled to the processor, the microphone and speaker configured to transmit sound.

13 Claims, 4 Drawing Sheets

VIDEO CONFERENCE SYSTEM

BACKGROUND

The present disclosure is directed to an improved video conference system for use with surgical implants, particularly from delivery of the surgical implants from the manufacture, including check-in to the hospital and finally from complete delivery to the surgical suite.

Medical Device Representatives sell surgical implants and provide surgical instruments to hospitals for use in the Operating room. Technology changes and improves at a fast pace so that it is not efficient for the hospital to own the instruments utilized for surgery. It is common practice for the instruments to be loaned to the hospital surgical team from the manufacturer for use to implant the device sold by the manufacturer.

Medical Device Representatives are invited to the Operating room as a service from the manufacturer to educate and explain the use of the instrument to the surgical team. Today more Medical Device Representatives are present in the operating room, and this produces infection, contamination, touching sterile field issues within the surgical suite.

What is needed is a technology that allows for a unique better solution, that provides the same service but without the Medical Device Representative physically present in the operating room.

SUMMARY

In accordance with the present disclosure, there is provided a system for video conference communication comprising a framework supporting a monitor; a processor operatively coupled with the monitor; a camera operatively coupled with the processor, wherein the framework is located in an operating room and the camera is configured to scan at least one of an instrument and an implant; and a microphone and speaker operatively coupled to the processor; the microphone and speaker being configured to transmit sound.

A further embodiment of any of the foregoing embodiments may additionally and/or alternatively include the system further comprising a remote-controlled laser pointer device.

A further embodiment of any of the foregoing embodiments may additionally and/or alternatively include the laser pointer is configured to identify the instrument and the implant remotely.

A further embodiment of any of the foregoing embodiments may additionally and/or alternatively include the laser pointer is configured to facilitate communication between a representative outside the operating room and a technician inside the operating room.

A further embodiment of any of the foregoing embodiments may additionally and/or alternatively include the framework is configured mounted to one of a wall, a ceiling, a table or a mobile cart.

A further embodiment of any of the foregoing embodiments may additionally and/or alternatively include the system further comprising a table including a sterile drape including reference marks configured to communicate instrument location on the table.

A further embodiment of any of the foregoing embodiments may additionally and/or alternatively include the system further comprising a control system including hardware, firmware, and/or software components.

A further embodiment of any of the foregoing embodiments may additionally and/or alternatively include a scale in operative communication with the control system, the scale configured to weigh instrument and implants.

A further embodiment of any of the foregoing embodiments may additionally and/or alternatively include at least one radio frequency identification tag coupled to at least one of the tray, the instrument and the implant.

In accordance with the present disclosure, there is provided a process for video conference communication comprising providing a framework supporting a monitor; a processor operatively coupled with the monitor, a camera operatively coupled with the processor, wherein the framework is located in an operating room and the camera is configured to scan at least one of an instrument and an implant; and a microphone and speaker configured to transmit sound into/out of the operating room; and checking contents of a surgical tray utilizing a software system.

A further embodiment of any of the foregoing embodiments may additionally and/or alternatively include the process further comprising verifying an identity of a representative; the manufacturer that representative represents; credentials of training for a particular surgical instrument/implant; the date and time of the surgery; the name of the surgeon; patient identification; and a purchase order or no charge purchase order.

A further embodiment of any of the foregoing embodiments may additionally and/or alternatively include the process further comprising documenting a weight of the surgical tray; and ensuring that before/after surgery all instruments and unused implants are returned without loss.

A further embodiment of any of the foregoing embodiments may additionally and/or alternatively include the process further comprising recording pictures of the surgical tray including the contents of the surgical tray.

A further embodiment of any of the foregoing embodiments may additionally and/or alternatively include the process further comprising prior to surgery, utilizing images and known weight, verifying a weight of all instruments/implants/devices that are included in the surgery.

A further embodiment of any of the foregoing embodiments may additionally and/or alternatively include the process further comprising recording a record of the surgical tray delivery; and a signature or verification to signify the surgical tray is safe complete and ready for surgery.

Other details of the system and process are set forth in the following detailed description and the accompanying drawings wherein like reference numerals depict like elements.

DETAILED DESCRIPTION

Referring now to the figures, a surgeon initiates a request to a Surgical Coordinator at the Hospital to invite a Medical Device representative (MDR™) or simply representative to attend a surgery.

There are various types of representatives. One type of representative is a direct employee of a particular manufacture. That representative only represents a particular company. Another type of representative includes a distributor. The distributor can represent multiple manufactures. Another type of representative includes a Stocking Distributor or Reseller. The Stocking Distributor or Reseller represents multiple manufactures.

Currently there is no verification of education for the representative concerning a level of training or expertise to represent the manufacturer or medical device product. A Hospital Vendor Passport™ would verify who the MDR™ is and what medical device/implant systems they represent and are trained on.

Once the representative is invited to the surgery, the instruments and implants are ordered from the manufacture who could provide initial pictures of sets to verify they are complete then shipped and delivered to the Hospital in Sterile processing where the representative can take pictures to compare the sets are complete. This is the final check to ensure all the instruments 10 and implants 12 are in place before sterilization.

Figure 1:
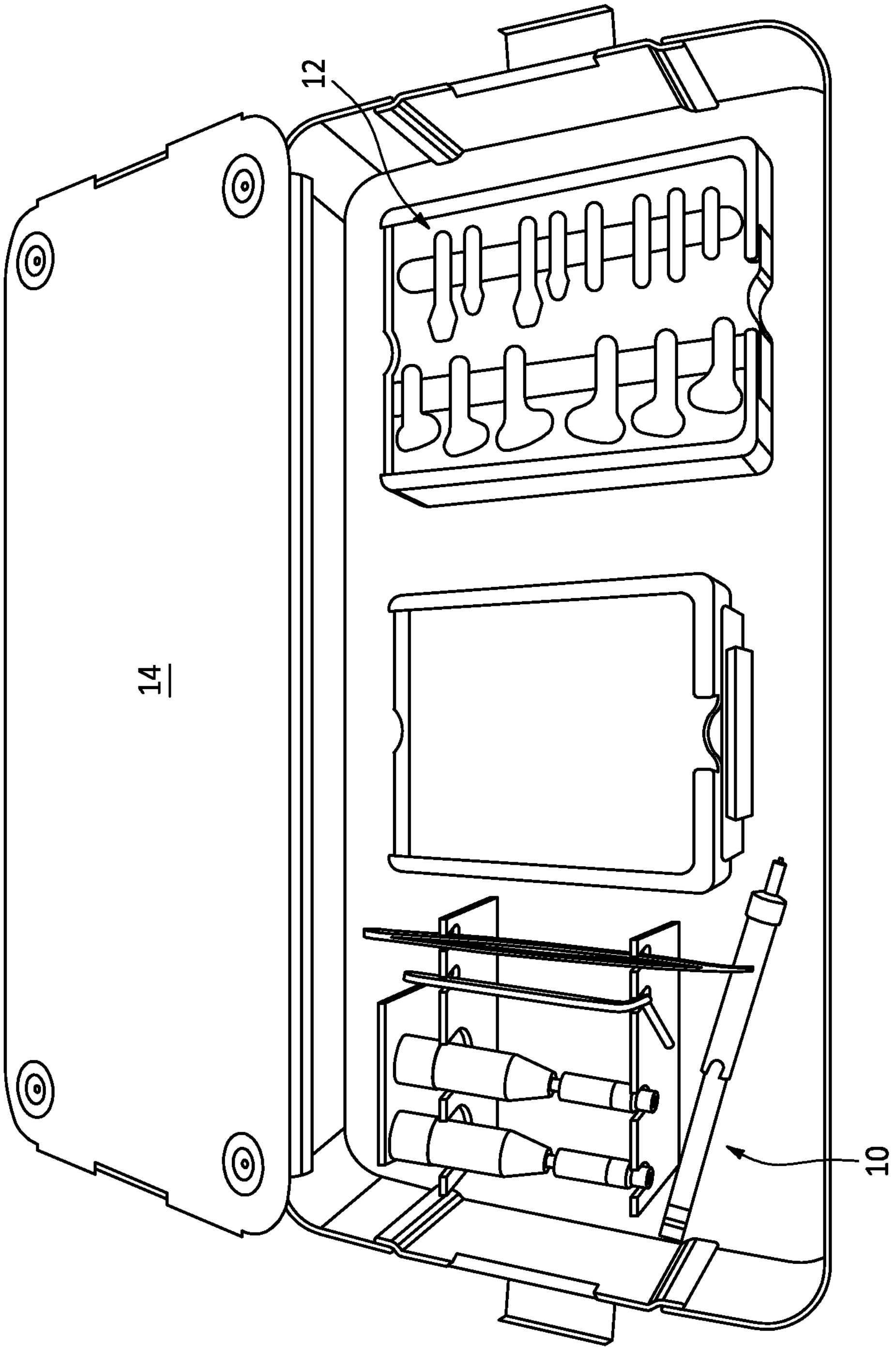
FIG. 1 is an image of a sample instrument tray.

Sterilization involves wrapping an instrument tray 14, see FIG. 1, in a wrapper or a container. The contents inside the wrapper or container are sterile while the outside is safe to touch. Multiple trays 14 may be needed for surgery. However, there is no verification and trackability to ensure all the required items are present in the tray 14.

The representative has the role of checking the contents of the tray 14 utilizing a software system designed for that function. The representative provides a signature verification that includes the identity of the representative; the manufacturer that they represent; credentials of training for a particular surgical instrument/implant; the date and time of the surgery; the name of the surgeon; patient identification (HIPPA compliant); and a purchase order or no charge purchase order.

The representative documents into the computer system the weight of each tray 14 as measured on a scale. Pictures of the tray 10 and the contents of the tray are recorded. The images and weight are utilized to provide verification of all instruments/implants/devices that are includes and ready for surgery. This level of detail ensures that before/after surgery all instruments 10 and unused implants 12 are returned without loss.

In exemplary embodiments, identity tags can be printed for verification and placed on the trays 14 after sterilization as the Hospital assumes responsibility for the sterilization.

At this point the surgical trays 14 are ready for surgery. A record of the surgical tray delivery and a signature or verification is recorded to signify the trays 14 are safe complete and ready for surgery. There is potentially provided a license number from the representative.

The representative is brought into the operating room to provide a service. The representative can educate, explain and demonstrate to the surgical team how to use and implant devices 12 for surgery. The representative can provide the list of implants 12 used and bill to the hospital.

Figure 3:
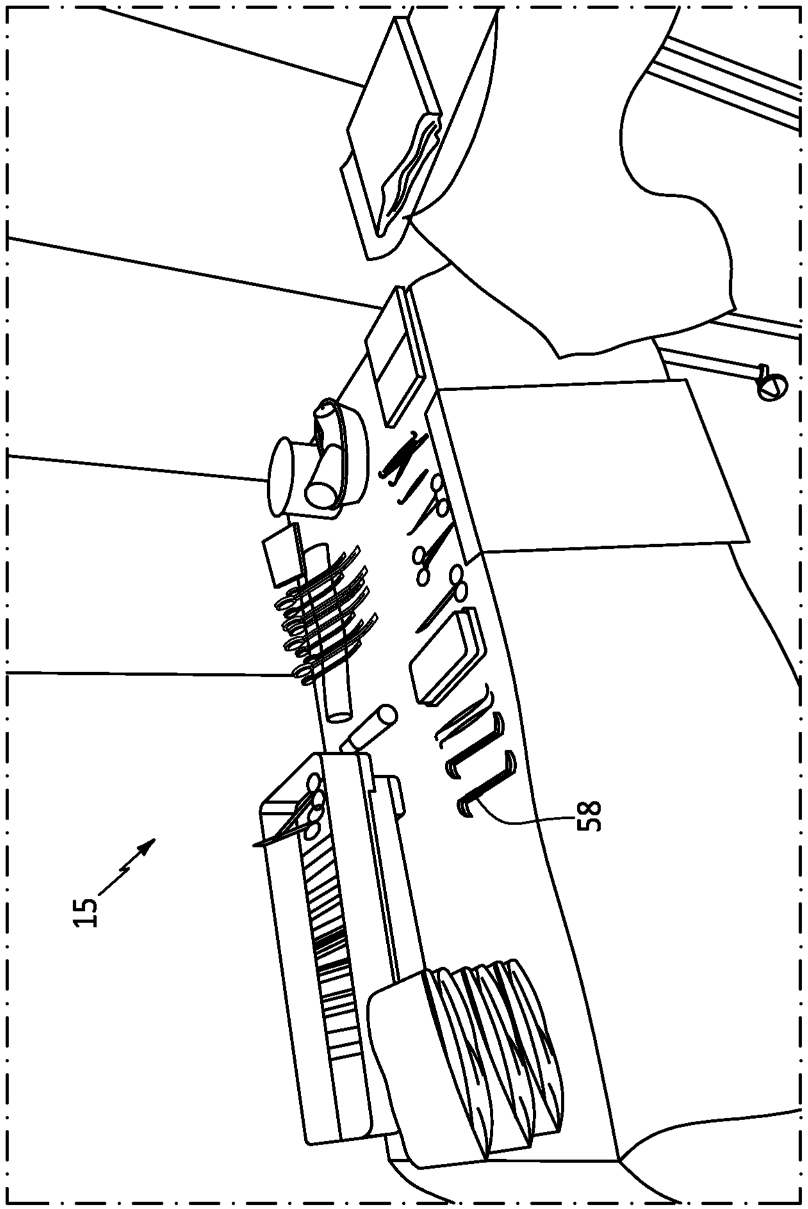
FIG. 3 is an image of an exemplary surgical table.
Figure 4:
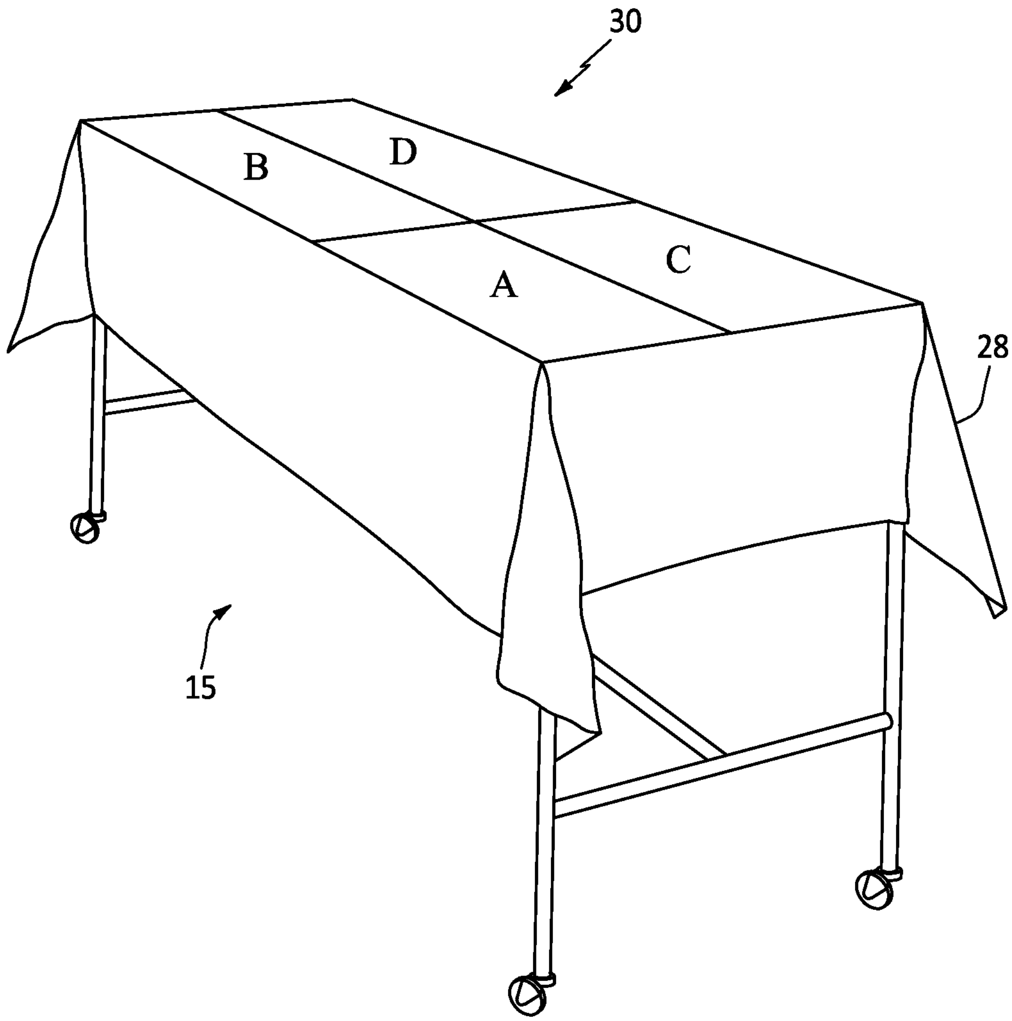
FIG. 4 is a schematic representation of an exemplary surgical drape for use with the exemplary mobile cart video conference device.

The representative cannot touch the patient, instruments 10 or implants 12. The representative can typically work with a Surgical tech to prepare the instruments 10 for the surgeon. The Surgical tech can touch the instruments 10 and implants 12. Much of the dialogue between the representative and Surgical tech can occur near an instrument/back table 15 as seen in FIGS. 3 and 4.

It is typical to have a TIME OUT verification in the operating room before the surgery starts. This is the time to ensure instruments 10 and implants 12 are ready for surgery. During the time out verification can include comparison to images.

Figure 2:
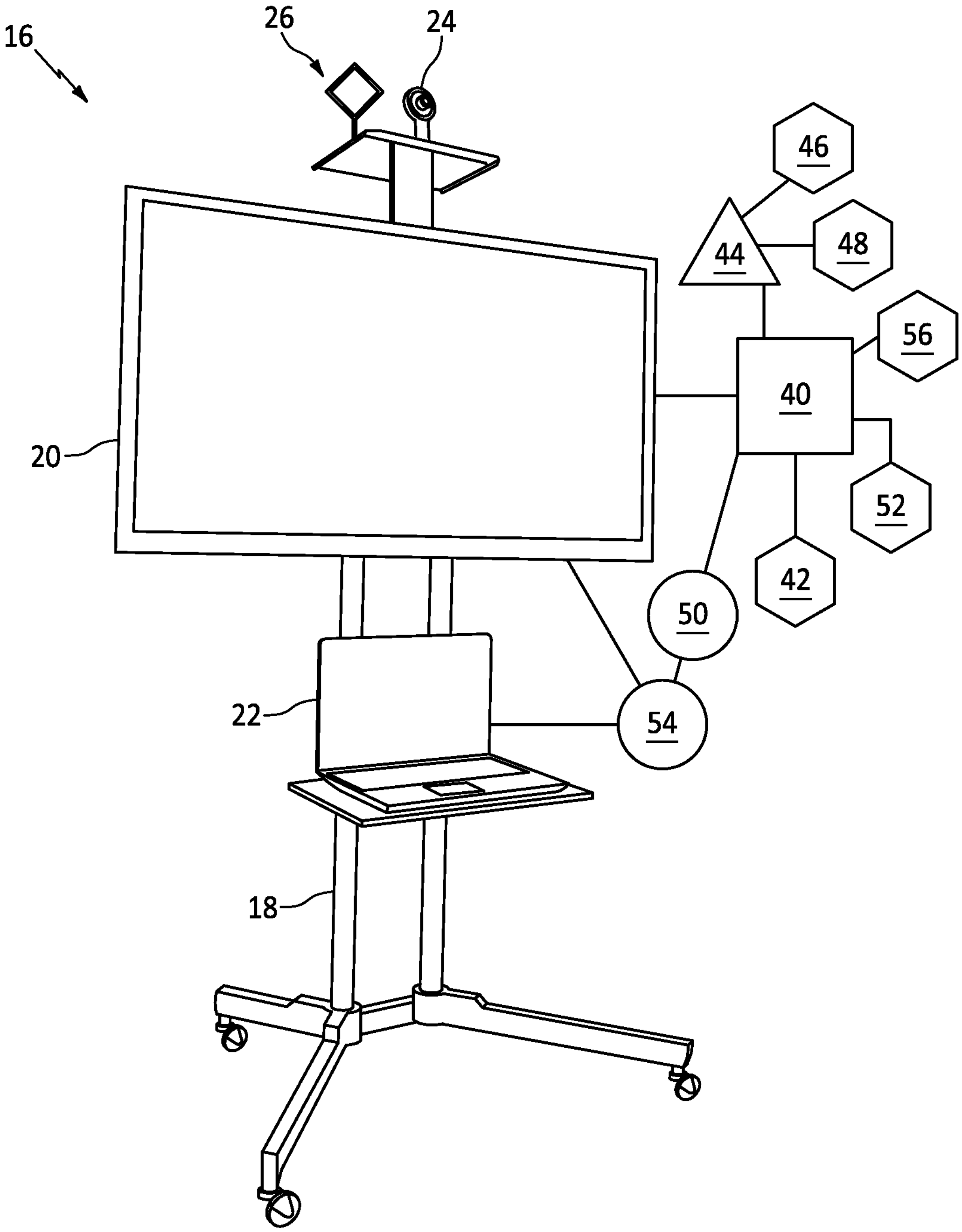
FIG. 2 is a schematic representation of an exemplary mobile cart video conference device.

As shown in FIG. 2, a video conference communication (VCC) device 16 can be utilized to facilitate the communication between the representative and the surgery personnel in the absence of the representative being located in the operating room. The VCC 16 includes a framework 18 supporting a monitor 20 in operative communication with a processor 22. The VCC 16 can include a camera 24 or sensor that can be configured to observe the instruments 10 and devices 12 that will be employed in the surgery. In an exemplary embodiment, the VCC 16 can include a remote-controlled laser pointer device 26. The laser pointer 26 can be employed by the representative to identify instruments 10 and implants/devices 12 by remote. The laser pointer 26 can be used to facilitate communication with the Surgery technician. The system could be used not just by sale representative but doctors as well.

In an exemplary embodiment, the camera 24 can be utilized to record pictures of the surgical tray 14 including the contents of the surgical tray 14 from manufacture, central processing, operating room, return from central processing and finally to the manufacture. This is very important to prevent loss of instruments 10, implants 12 to ensure what has been implanted to prevent billing questions and prevention of litigation on what was implanted and prepared for surgery.

A sterile drape can cover the VCC 16 as not to effect sterile field.

The VCC 16 can facilitated HIPPA compliant video conferencing that is not in person, face to face. The representative is removed from the operating room. This eliminates infection, contamination, and Operating room traffic.

Instead, the communication is face to back table 15. This way the representative can see the instruments 10 and trays 14. The representative can be located onsite at the Hospital or another location or even a call center.

Verification and images of the instruments 10 and devices/implants 12 can be provided on the monitor 20 to be viewed by the representative. The representative and Surgery technician can perform a picture verification for the instruments 10 that were delivered and compare the instruments 10 in view on the back table 15.

Utilizing the VCC 16, multiple representatives can be in que ready for the surgeon without the need to be located in the operating room. The use of the VCC 16 allows for the representative to cover other cases in other operating rooms until being needed.

The VCC 16 is shown configured as a portable cart, it is contemplated that the VCC system 16 could be mounted to a wall, ceiling, table or mobile cart. The main feature of the VCC 16 is the configuration of the camera 24 positioned to view of the instrument table 15.

In an exemplary embodiment, the instrument/back table 15 can include a sterile drape 28 including reference marks 30 to allow for better communication of instrument location on the table 15. The reference marks as shown can be A, B, C and D. Other marking can be used such as alpha/numerical marking, symbols, and combinations thereof.

The surgical drape with marking allows for the representative to have position points to help identify to the Surgical tech where an instrument 10 might be located on the table 15. The representative can employ the remote-controlled laser pointer 26 to show the location of the instrument 10 or device/implant 12; as this does not affect the sterile field.

The VCC 16 allows the representative to see the hands and what the Surgical tech is assembling. The monitor 20 allows the Surgical tech to see the representative and visuals to copy. The VCC system 16 allows for the implants 12 to be recorded by the representative and sent to the following but not limited to: Patient record; Implant removal registry; Hospital data base; Billing; TSA—medical device record and the like. Before/after surgery there is a visual record of the instruments 10 that were delivered to show the cycle is complete and the instruments 10 and unused implants 12 can be returned to the manufacturer.

The VCC 16 can include a control system 40 may include hardware, firmware, and/or software components that are configured to perform the functions disclosed herein, including the functions of the VCC 16. While not specifically shown, the control system 40 may include other computing devices (e.g., servers, mobile computing devices, etc.) and computer aided manufacturer (CAM) systems which may be in communication with each other and/or the control system 40 via a communication network 42 to perform one or more of the disclosed functions. The control system 40 may include at least one processor 44 (e.g., a controller, microprocessor, microcontroller, digital signal processor, etc.), memory 46, and an input/output (I/O) subsystem 48. The control system 40 may be embodied as any type of computing device e.g., a server, an enterprise computer system, a network of computers, a combination of computers and other electronic devices, or other electronic devices. Although not specifically shown, the I/O subsystem 48 typically includes, for example, an I/O controller, a memory controller, and one or more I/O ports. The processor 44 and the I/O subsystem 48 are communicatively coupled to the memory 46. The memory 46 may be embodied as any type of computer memory device (e.g., volatile memory such as various forms of random access memory).

The I/O subsystem 48 is communicatively coupled to a number of hardware, firmware, and/or software components, including a data storage device 50, the display 20, a communication subsystem 52, a user interface (UI) subsystem 54. The data storage device 50 may include one or more hard drives or other suitable persistent storage devices (e.g., flash memory, memory cards, memory sticks, and/or others).

The display 20 may be embodied as any type of digital display device, such as a liquid crystal display (LCD), and may include a touchscreen. The display 20 is configured or selected to be capable of displaying two- and/or three-dimensional graphics. The communication subsystem 52 may include one or more optical, wired, and/or wireless network interface subsystems, cards, adapters, or other devices, as may be needed pursuant to the specifications and/or design of the particular computing device. The user interface subsystem 54 may include one or more user input devices (e.g., the display 20, a microphone, a touchscreen, keyboard, virtual keypad, etc.) and one or more output devices (e.g., audio speakers, LEDs, additional displays, etc.) to facilitate the communication between the representative and the personnel in the operating room. A scale 56 can be operatively coupled to the control system 40 for use in weighing the instruments 10 and implants 12. At least one radio frequency identification tag (RFID) 58 can be coupled to at least one of the tray 14, instrument 10 and implant 12. The RFID tag system 58 for instrument 10 and implant 12 can further use AI to locate missing instrument can be deployed.

A technical advantage of the disclosed video conference communication system includes elimination of infection, contamination, and Operating room traffic.

Another technical advantage of the disclosed video conference communication system includes utilization of the system by multiple representatives without the need to be located in the operating room.

Another technical advantage of the disclosed video conference communication system includes coverage of multiple surgery cases in multiple locations by a representative.

There has been provided a system and process. While the system and process have been described in the context of specific embodiments thereof, other unforeseen alternatives, modifications, and variations may become apparent to those skilled in the art having read the foregoing description. Accordingly, it is intended to embrace those alternatives, modifications, and variations which fall within the broad scope of the appended claims.

What is claimed is:

1. A system for video conference communication comprising:

a framework supporting a monitor;

a processor operatively coupled with the monitor a camera mounted to the framework operatively coupled with the processor, wherein said framework is located in an operating room and said camera is configured to scan at least one of an instrument and an implant;

a microphone and speaker mounted to the framework operatively coupled to said processor, the microphone and speaker being configured to transmit sound; and a table including a sterile drape including reference marks configured to communicate instrument location on the table, the reference marks comprise alpha/numeric marking, symbols and combinations thereof, wherein the sterile drape with reference marks is configured to indicate a predetermined position of an instrument on position points to help identify where an instrument is located.

2. The system according to claim 1, further comprising:

a remote-controlled laser pointer device mounted to the framework.

3. The system according to claim 2, wherein the laser pointer is configured to identify the instrument and the implant remotely.

4. The system according to claim 2, wherein the laser pointer is configured to facilitate communication between a representative outside the operating room and a technician inside the operating room.

5. The system according to claim 1, wherein the framework is configured mounted to one of a wall, a ceiling, a table or a mobile cart.

6. The system according to claim 1, further comprising:

a control system including hardware, firmware, and/or software components.

7. The system according to claim 6 further comprising:

a scale in operative communication with the control system, the scale configured to weigh instrument and implants.

8. The system according to claim 1, further comprising:

at least one radio frequency identification tag coupled to at least one of the tray, the instrument and the implant.

9. A process for video conference communication comprising:

providing a framework supporting a monitor;

a processor operatively coupled with the monitor a camera mounted on the framework operatively coupled with the processor, wherein said framework is located in an operating room and said camera is configured to scan at least one of an instrument and an implant;

a microphone and speaker mounted on the framework configured to transmit sound;

checking contents of a surgical tray utilizing a software system;

identifying a location of an instrument on a sterile drape on a table including the sterile drape, the sterile drape including reference marks configured to communicate instrument location on the table, wherein the reference marks include alpha/numeric marking, symbols and combinations thereof;

recording a record of the surgical tray delivery; and recording a signature to signify the surgical tray is safe complete and ready for surgery.

10. The process of claim 9, further comprising:

verifying an identity of a representative; the manufacturer that representative represents; credentials of training for a particular surgical instrument/implant; the date and time of the surgery; the name of the surgeon; patient identification; and a purchase order or no charge purchase order.

11. The process of claim 9, further comprising:

documenting a weight of the surgical tray; and ensuring that before/after surgery all instruments and unused implants are returned without loss.

12. The process of claim 9, further comprising:

recording pictures of the surgical tray including the contents of the surgical tray.

13. The process of claim 9, further comprising:

prior to surgery, utilizing images and known weight, verifying a weight of all instruments/implants/devices that are included in the surgery.

* * * * *